United States Patent
Ben-Shlomo et al.

(10) Patent No.: US 8,709,804 B2
(45) Date of Patent: Apr. 29, 2014

(54) METHOD FOR DRUG SCREENING AND CHARACTERIZATION BY CALCIUM FLUX

(75) Inventors: Anat Ben-Shlomo, Beverly Hills, CA (US); Shlomo Melmed, Los Angeles, CA (US); Kolja Wawrowsky, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 999 days.

(21) Appl. No.: 11/719,085

(22) PCT Filed: Dec. 21, 2005

(86) PCT No.: PCT/US2005/046468
§ 371 (c)(1),
(2), (4) Date: Feb. 11, 2008

(87) PCT Pub. No.: WO2006/069188
PCT Pub. Date: Jun. 29, 2006

(65) Prior Publication Data
US 2008/0253641 A1    Oct. 16, 2008

Related U.S. Application Data

(60) Provisional application No. 60/638,340, filed on Dec. 21, 2004.

(51) Int. Cl.
*C12N 5/00*    (2006.01)
(52) U.S. Cl.
USPC .............................................. 435/375; 435/4
(58) Field of Classification Search
USPC .................................................. 435/4, 375
See application file for complete search history.

(56) References Cited

U.S. PATENT DOCUMENTS

| | | | |
|---|---|---|---|
| 5,383,023 A | 1/1995 | Walleczek | |
| 5,767,129 A | 6/1998 | Yuen | |
| 6,245,329 B1 | 6/2001 | Kelner et al. | |
| 6,686,193 B2 | 2/2004 | Maher et al. | |
| 2001/0033841 A1 | 10/2001 | Luster et al. | |
| 2003/0044389 A1 | 3/2003 | Brown et al. | |
| 2004/0009537 A1 | 1/2004 | Roos et al. | |
| 2004/0018567 A1 | 1/2004 | Vallone et al. | |
| 2004/0110244 A1 | 6/2004 | DeBernardi et al. | |

FOREIGN PATENT DOCUMENTS

| | | |
|---|---|---|
| JP | 2000338045 | 12/2000 |
| WO | 9641166 | 12/1996 |
| WO | 02/101339 A2 | 12/2002 |

OTHER PUBLICATIONS

Mahoney et al. "Independent pathways regulate the cytosolic [Ca2+] initial transient and subsequent oscillations in individual cultured arterial smooth muscle cells responding to extracellular ATP", Molecular Biology of the Cell, 1992, 3:493-505.*
Novak et al. "Purinergic receptors have different effects in rat exocrine pancreas. Calcium signals monitored by Fura-2 using confocal microscopy", Cellular Physiology and Biochemistry, 2002, 12:83-92.*
Wokosin et al., Characterization of a Range of Fura Dyes with Two-Photon Excitation, Biophysical Journal, (Mar. 2004), pp. 1726-1738, 86.
Luo et al., Signaling Pathways Underlying Muscarinic Receptor-Induced [Ca2+]i Oscillations in HEK293 Cells, The Journal of Biological Chemistry, (Feb. 23, 2001), pp. 5613-5621, 276(8).
Stosiek et al., In Vivo Two-Photon Calcium Imaging of Neuronal Networks, PNAS, (Jun. 10, 2003), pp. 7319-7324, 100(12).
Bird et al., Capacitative Calcium Entry Supports Calcium Oscillations in Human Embryonic Kidney Cells, Journal of Physiology, (2005), pp. 697-706, 562.3.
Peterson et al., The Patch-Clamp Technique: Recording Ionic Currents Through Single Pores in the Cell Membrane, NIPS, (Feb. 1986), pp. 5-8, 1.
Knight et al., Live Cell Imaging Using Confocal Microscopy Induces Intracellular Calcium Transients and Cell Death, American Journal of Physiology, (2003), pp. C1083-C1089, 284.
Office Action dated Sep. 16, 2010 in JP 2007-548446.
Abstract of Japanese Publication No. 2003-227796 published Aug. 15, 2008 (Zeiss Carl Jena GMBH).
Japanese Publication No. 2004-522163 published Jul. 22, 2004 (English abstract not available), corresponds to WO2002/101339 published Dec. 19, 2002.
Abstract of Japanese Publication No. 2004-294107 published Oct. 21, 2004 (Mitsui Eng. & Shipbuild Co. Ltd.).
Japanese Publication No. 11-508355 published Jul. 21, 1999 (English abstract not available), corresponds to WO1996/41166 (PCT publication WO1996/41166 already submitted in an IDS filed Jul. 28, 2010).
Office Action dated Jun. 2, 2010 in JP 2007-548446.

* cited by examiner

*Primary Examiner* — Bin Shen
(74) *Attorney, Agent, or Firm* — Brian T. Duke; Nixon Peabody LLP

(57) ABSTRACT

The instrumentation and methods described herein are based on imaging and measuring single cell dose response by fluorescent ion imaging that records live cell responses to drug doses. Dose response curves and other pharmacological parameters can be computed by imaging and measuring oscillation changes for each drug dose and each cell. The instrumentation and methods described herein provide a means of measuring statistical variability of cell populations for improved screening and development methods for drugs.

22 Claims, 14 Drawing Sheets

METHOD FOR DRUG SCREENING AND CHARACTERIZATION BY CALCIUM FLUX

CROSS-REFERENCE TO RELATED APPLICATIONS

This application is the National Phase of International Application PCT/US05/46468, filed Dec. 21, 2005, which designated the U.S. and that International Application was published under PCT Article 21(2) in English. This application also includes a claim of priority under 35 U.S.C. §119(e) to U.S. provisional patent application No. 60/638,340, filed Dec. 21, 2004.

FIELD OF THE INVENTION

The present invention relates generally to the field of drug discovery; more particularly, to instrumentation and methods of analyzing ion oscillations to screen compounds.

BACKGROUND OF THE INVENTION

Ions move across plasma membranes and organelle membranes through channels created by proteins, which allows for the formation of concentration gradients between exterior and interior compartments. Ion channels participate in, and regulate, cellular processes as diverse as the generation and timing of action potentials, energy production, synaptic transmission, secretion of hormones and the contraction of muscles. In fact, many drugs exert their specific effects via modulation of ion channels. Examples include antiepileptic compounds like phenyloin and lamotrigine, which block voltage-dependent sodium channels in the brain, antihypertensive drugs like nifedipine and diltiazem, which block voltage-dependent calcium channels in smooth muscle cells, and stimulators of insulin release like glibenclamide and tolbutamide, which block ATP-regulated potassium channels in the pancreas.

There are many types of ion channels including, for example, ligand-gated channels, which open or close in response to the binding of signalling molecules; cyclic nucleotide-gated channels, which open in response to internal solutes and mediate cellular responses to second messengers; Stretch-activated channels, which open or close in response to mechanical forces that arise from local stretching or compression of the membrane; G-protein-gated channels, which open in response to G protein-activation via its receptor; and voltage-gated channels, which open or close in response to changes in the charge across the plasma membrane.

Finding new drugs which have specific modulatory effects on ion channels requires methods for measuring and manipulating the membrane potential and/or concentration gradient of cells with the ion channels present in the membrane. A number of methods exist that can be used to measure cell transmembrane potentials and/or concentration gradients and to measure the activities of specific ion channels. For example, patch-clamp recording was the first technique capable of monitoring the function of single biological molecules by measurement of single-channel currents (Neher, E. and B. Sakmann, "Single-channel currents recorded from membrane of denervated frog muscle fibres," *Nature (London)*, 260:799-802 (1976); Hamill, O. P. et al., "Improved patch-clamp techniques for high-resolution current recording from cells and cell-free membrane patches," *Pflugers Arch.*, 391:85-100 (1981)). Using the patch-clamp technique, the properties of ion channels can be studied by means of a very fine pipette (with an opening of about 0.5 µm) that is pressed against the plasma membrane of either an intact cell or that is used to pull away the plasma membrane from the cell and the preparation placed in a test solution of desired composition. In so doing, current flow through a single ion channel can then be measured. Techniques are known in the art for performing patch-clamp techniques that are suitable (Petersen, O. H. et al., "The Patch-Clamp Technique: Recording Ionic Currents Through Single Pores in the Cell Membrane," *Physiology*, 1(1):5-8 (1986); Boulton, A. A. et al., Patch-Clamp Applications and Protocols, Vol. 26 (1995)). For example, common techniques may include performing cell-free ion-channel recording, the whole-cell patch clamp technique, concentration clamp technique, the pressure clamp method, the perfusion of patch clamp electrodes, loose patch-clamp technique, single-channel recording and the perforated patch-clamp technique. However, a major limitation of the patch clamp technique as a general method in pharmacological screening is its low throughput. Typically, a single, highly trained operator can test fewer than ten compounds per day using the patch clamp technique. Furthermore, the technique is not easily amenable to automation, and produces complex results that require extensive analysis by skilled electrophysiologists.

The use of optical detection systems provides for significantly greater throughput for screening applications and advances in optical techniques have allowed direct visualization of calcium signaling at the cellular and subcellular level (Lino, R. et al., "Single molecule imaging of green fluorescent proteins in living cells: E-cadherin forms oligomers on the free cell surface," *Biophys. J.*, 80:2667-2677 (2001); Schnitzer, M. J. et al., "Force production by single kinesin motors," *Nat. Cell Biol.*, 10:718-723 (2000); Sonnleitner, A. et al., "Structural rearrangements in single ion channels detected optically in living cells," *Proc. Natl. Acad. Sci. U.S.A.*, 99:12759-12764 (2002); Zou, H. et al., "Imaging $Ca^{21}$ entering the cytoplasm through a single opening of a plasma membrane cation channel," *J. Gen. Physiol.*, 114:575-588 (1999); Zou, H. et al., "Visualization of $Ca^{21}$ entry through single stretch-activated cation channels," *Proc. Natl. Acad. Sci. U.S.A.*, 99:6404-6409 (2002); Wang, S. Q. et al., "$Ca^{21}$ signalling between single L-type $Ca^{21}$ channels and ryanodine receptors in heart cells," *Nature (London)*, 410: 592-596 (2001); Demuro, A. and I. Parker, "Optical single channel recording: imaging $Ca^{21}$ flux through individual N-type voltage-gated channels expressed in *Xenopus* oocytes," *Cell Calcium*, 34:499-509 (2003); Demuro, A. and I. Parker, "Imaging the activity and localization of single voltage-gated $Ca^{21}$ channels by total internal reflection fluorescence microscopy," *Biophys. J.*, 86:3250-3259 (2004).) Indeed, advances in the development of video imaging and confocal microscopy, have led to the discovery of polarized, subcellular calcium signals in various cell types (Knot, H. J. et al., "Twenty Years of Calcium Imaging: Cell Physiology to Die For," *Mol. Interv.* 5:112-127 (2005)). The shape of intracellular calcium signals (i.e., amplitude and frequency) is determined by the distribution of calcium-releasing channels and mechanisms that limit calcium elevation (Jiang, Y. et al., "Numerical Simulation of Ca2+ 'Sparks' in Skeletal Muscle," *Biophys J* 77(5): 2333-2357 (1999)). In addition, development of new cell permeable fluorescent reporters, such as luminescent photoproteins, fluorescent proteins and fluorescent dyes, has opened the way for dynamic cellular assays by allowing activity at drug targets to be determined in living cells (Zhang, J. et al., "Creating New Fluorescent Probes for Cell Biology," *Nature* 3:906-918 (2002)). For example, one optical method of analysis has been previously described (Gonzalez and Tsien, "Improved indicators of cell membrane potential that use fluorescence resonance energy transfer,"

*Chemistry and Biology,* 4(4):269-277 (1997); Gonzalez and Tsien, "Voltage sensing by fluorescence resonance energy transfer in single cells," *Biophysical Journal,* 69:1272-1280 (1995); and U.S. Pat. No. 5,661,035), that comprises two reagents that undergo energy transfer to provide a ratiometric fluorescent readout that is dependent upon the membrane potential. The ratiometric readout provides important advantages for drug screening including improved sensitivity, reliability and reduction of many types of experimental artifacts.

As currently practiced in the art, drug discovery is a long and multiple step process involving identification of specific disease targets, development of an assay based on a specific target, validation of the assay, optimization and automation of the assay to produce a screen, high throughput screening of compound libraries using the assay to identify "hits", hit validation and hit compound optimization. The output of this process is a lead compound that goes into pre-clinical and, if validated, eventually into clinical trials. In this process, the screening phase is distinct from the assay development phases, and involves testing compound efficacy in living biological systems.

Bioinformatics, genomics, proteomics and high throughput screening have become indispensable in identifying potential new drug targets, predicting drug interactions, and increasing capacity and efficiency in the areas of target identification. However, even with these developing technologies, there is a need to measure multi-dimensional information from cells and a need for tools that provide increased information handling capability. These aspects of drug discovery make the observation of ion fluctuation particularly suitable to measuring multiple parameters of cell response to compound administration. Indeed, optical imaging methods for screening large numbers of compounds are known in the art (See, e.g., U.S. Pat. No. 6,875,578).

The conventional measurement in early drug discovery assays was radioactivity. However, the need for more information, higher throughput and miniaturization has caused a shift towards using fluorescence detection. Fluorescence-based reagents can yield more powerful, multiple parameter assays that are higher in throughput and information content and require lower volumes of reagents and test compounds. Fluorescence is also safer and less expensive than radioactivity-based methods. The types of biochemical and molecular information now accessible through fluorescence-based reagents applied to cells include ion concentrations, membrane potential, specific translocations, enzyme activities, gene expression, as well as the presence, amounts and patterns of metabolites, proteins, lipids, carbohydrates, and nucleic acid sequences (DeBiasio, R. L. et al., "Myosin II transport, organization, and phosphorylation: evidence for cortical flow/solution-contraction coupling during cytokinesis and cell locomotion," *Mol. Biol. Cell.,* 7(8):1259-82 (1996); Heim, R. and Tsien, R. Y., "Engineering green fluorescent protein for improved brightness, longer wavelengths and fluorescence resonance energy transfer," *Curr. Biol.* 6(2): 178-82 (1996)).

Conventional means of imaging fluorescent samples provide calculations of total fluorescence average over a cell sample. For example, Science Applications International Corporation (SAIC) (Seattle, Wash.) describes an imaging plate reader that uses a CCD camera to image the whole area of a 96 well plate. The image is analyzed to calculate the total fluorescence per well for all the material in the well. Similarly, Molecular Devices, Inc. (Sunnyvale, Calif.) describes a system (FLIPR) which uses low angle laser scanning illumination and a mask to selectively excite fluorescence within approximately 200 microns of the bottoms of the wells in standard 96 well plates in order to reduce background when imaging cell monolayers. This system uses a CCD camera to image the whole area of the plate bottom. Although this system measures signals originating from a cell monolayer at the bottom of the well, the signal measured is averaged over the area of the well and is therefore still considered a measurement of the average response of a population of cells. The image is analyzed to calculate the total fluorescence per well for cell-based assays. Fluid delivery devices have also been incorporated into cell based screening systems, such as the FLIPR system, in order to initiate a response, which is then observed as a whole well population average response using a macro-imaging system.

However, cell populations are biologically heterogeneous, and the high spatial and temporal frequency of chemical and molecular information present within cells makes it impossible to extract high-content information from populations of cells using conventional techniques. Indeed, conventional techniques for monitoring and analyzing, for example, ion oscillations using fluorescence has substantial drawbacks; for example, photobleaching and lack of specific information concerning individual cells. Conventional techniques also are not fast or cost-efficient; for example, dose-dependent experiments using the patch-clamp technique typically require two days to complete.

In contrast to high throughput screens, high-content screens have also been developed to address the need for more detailed information about the temporal-spatial dynamics of cell constituents and processes. High-content screens automate the extraction of multicolor fluorescence information derived from specific fluorescence-based reagents incorporated into cells (Giuliano, K. A. and Taylor D. L., "Measurement and manipulation of cytoskeletal dynamics in living cells," *Curr Opin Cell Biol.,* 7(1):4-12 (1995)). Cells are analyzed using optical systems that can measure spatial and temporal dynamics (Farkas, D. L. et al., "Multimode light microscopy and the dynamics of molecules, cells, and tissues," *Ann. Rev. Physiol.,* 55:785-817 (1993)). With high-content screening, the concept is to treat each cell as a "well" that has spatial and temporal information on the activities of the labeled constituents. High-content screens can be performed on either fixed cells, using fluorescently labeled antibodies, biological ligands, and/or nucleic acid hybridization probes, or live cells using multicolor fluorescent indicators and "biosensors." The choice of fixed or live cell screens depends on the specific cell-based assay required. Fixed cell assays provide an array of initially living cells in a microtiter plate format which can be treated with various compounds and doses being tested. Thereafter, cells can be fixed, labeled with specific reagents, measured and no environmental control of the cells is required after fixation. In this way, spatial information is acquired at one time point. Live cell assays provide an array of living cells containing the desired reagents which can be screened over time and space. Environmental control of the cells (temperature, humidity, and carbon dioxide) is required during measurement, since the physiological health of the cells must be maintained for multiple fluorescence measurements over time. Fluorescent physiological indicators and "biosensors" can report changes in biochemical and molecular activities within cells (Hahn et al., In Fluorescent and Luminescent Probes for Biological Activity, W. T. Mason (ed.), pp. 349-359 (1993) Academic Press, San Diego).

Scanning confocal microscope imaging (Go, W. Y. et al., "Quantitative dynamic multicompartmental analysis of cholecystokinin receptor movement in a living cell using dual fluorophores and reconstruction of confocal images," *Anal*

Biochem., 247(2):210-215 (1997)) and multiphoton microscope imaging (Denk, W. et al., "Two-photon laser scanning fluorescence microscopy," *Science*, 248:73-6 (1990)) are well established methods for acquiring high resolution images of microscopic samples. These optical systems provide for shallow depth of focus, which allows features of limited axial extent to be resolved against the background. For example, it is possible to resolve internal cytoplasmic features of adherent cells from the features on the cell surface. Because scanning multiphoton imaging requires very short duration pulsed laser systems to achieve the high photon flux required, fluorescence lifetimes can also be measured in these systems (Lakowicz, J. R. et al., "Fluorescence lifetime imaging," Anal Biochem., 202:316-330 (1992)), providing additional capability for different detection modes. However, these imaging methods are limited by the efficiency, photostability and toxicity of the fluorescence in the chosen system. Thus, there remains a need in the art for instrumentation and methods to directly measure ion oscillations of individual cells in a sample that results from dose-dependent administration of a compound.

One example of ion oscillation occurs in calcium ($Ca^{2+}$) channels, which are generally found in many cells where, among other functions, they play important roles in signal transduction. In excitable cells, intracellular calcium supplies a maintained inward current for long depolarizing responses and serves as the link between depolarization and other intracellular signal transduction mechanisms. Like voltage-gated sodium channels, voltage-gated calcium channels have multiple resting, activated, and inactivated states.

Calcium channel antagonists are potent vasodilators and are widely used in the treatment of hypertension and angina pectoris. Clinically approved compounds in the United States include, for example, dihydropyridines (e.g., amlodipine, felodipine, nifedipine, nicardipine, isradipine, nimodipine); benzothiazepines (e.g., diltiazem), phenylalkylamines (e.g., verapamil); and diarylaminopropylamine ether (e.g., bepridil) (See, e.g., U.S. Pat. No. 6,897,305).

Endocrine cells, including gonadotroph, somatotroph, and corticotroph cells, exhibit baseline spontaneous calcium oscillations (BSCOs) in vitro as well as in their native environment (Bonnefont, X. et al., "Rhythmic bursts of calcium transients in acute anterior pituitary slices," *Endocrinology*, 141(3):868-75 (2000); Kwiecien, R. et al., "Differential management of Ca2+ oscillations by anterior pituitary cells: a comparative overview," *Neuroendocrinology* 68:135-151 (1998); Kaftan, E. J. et al., "Mitochondria shape hormonally induced cytoplasmic calcium oscillations and modulate exocytosis," *J Biol Chem* 275:25465-25470 (2000); Schlegel, W. et al., "Oscillations of cytosolic Ca2+ in pituitary cells due to action potentials. *Nature* 329:719-721 (1987); Charles, A. C. et al., "L-type Ca2+ channels and K+ channels specifically modulate the frequency and amplitude of spontaneous Ca2+ oscillations and have distinct roles in prolactin release in GH3 cells," *J Biol Chem* 274:7508-7515 (1999); Surprenant, A., "Correlation between electrical activity and ACTH/beta-endorphin secretion in mouse pituitary tumor cells," *J Cell Biol* 95:559-566 (1982); Adler, M. et al., "Intracellular calcium and hormone secretion in clonal AtT-20/D16-16 anterior pituitary cells," *Cell Calcium* 10:467-476 (1989); Thomas, P., and Smith, P. A., "Tetrabutylammonium: a selective blocker of the somatostatin-activated hyperpolarizing current in mouse AtT-20 corticotrophs," *Pflugers Arch* 441:816-823 (2001); Fiekers, J. F., and Konopka, L. M., "Spontaneous transients of [Ca2+]i depend on external calcium and the activation of L-type voltage-gated calcium channels in a clonal pituitary cell line (AtT-20) of cultured mouse corticotropes," *Cell Calcium* 19:327-336 (1996); Maturana, A. et al., "Spontaneous calcium oscillations control c-fos transcription via the serum response element in neuroendocrine cells. *J Biol Chem* 277:39713-39721 (2002)). Minor differences in baseline and stimulated calcium oscillation patterns have been noted between normal corticotroph and AtT-20 cells (Kwiecien 1998). Baseline spontaneous calcium oscillations may represent the sum of cellular calcium channels mediating replenishment and maintenance of calcium concentrations required for intact calcium dependent signaling pathways and cellular homeostasis (Gill, D. L., and Patterson, R. L., "Toward a consensus on the operation of receptor-induced calcium entry signals," *Sci STKE* 2004:39 (2004)). Their importance for regulation of ACTH secretion has also been described (Kwiecien 1998; Adler 1989; Tse, A., and Lee, A. K., "Voltage-gated Ca2+ channels and intracellular Ca2+ release regulate exocytosis in identified rat corticotrophs," *J Physiol* 528(1):79-90 (2000)). Understanding these oscillations and their underlying mechanisms is important for cellular physiology as well as screening for novel drug treatments (Berridge, M. J. et al., "The versatility and universality of calcium signaling," *Nat Rev Mol Cell Biol*, 1(1):11-21 (2000)).

Calcium oscillations are caused by repetitive periodic release of calcium from internal stores and subsequent recharging. Generally, calcium release-activated calcium channels (CRAC) as well as arachidonate-regulated calcium channels (ARC) contribute to oscillations (Shuttleworth, T. J. and O. Mignen, "Calcium entry and the control of calcium oscillations," *Biochem Soc Trans*, 31(5):916-9 (2003)). However, at low agonist concentrations, ARC channels dominate calcium oscillations. In contrast, at higher concentrations, depletion of calcium stores becomes more profound and activation of CRAC channels leads to constantly elevated levels.

The different types of calcium channels have been broadly categorized into four classes, L-, T-, N-, and P-type, distinguished by current kinetics, holding potential sensitivity and sensitivity to calcium channel agonists and antagonists. L-type calcium channel antagonists such as nimodipine block spontaneous oscillations in AtT-20 clonal pituitary cells (Fiekers, J. F. and L. M. Konopka, "Spontaneous transients of [$Ca^{2+}$]i depend on external calcium and the activation of L-type voltage-gated calcium channels in a clonal pituitary cell line (AtT-20) of cultured mouse corticotropes," *Cell Calcium*, 19(4):327-36 (1996)). In contrast, voltage-gated sodium channels are not involved in spontaneous calcium oscillations (Fiekers 1996). Moreover, while AtT-20 cells have been shown to have T-type and L-type channels, only L-type channel antagonists reversibly block oscillations (Fiekers 1996). Indeed, activation of L-type channels produces large, transient and sustained calcium oscillations (Fiekers 1996). Changes in oscillation patterns have also been studied in AtT-20 cells in response to norepinephrine and somatostatin (Adler, M. et al., "Intracellular calcium and hormone secretion in clonal AtT-20/D16-16 anterior pituitary cells," *Cell Calcium*, 10(7):467-76 (1989)).

Calcium channels mediate the influx of $Ca^{2+}$ into cells in response to changes in membrane potential and/or concentration gradient, and because of their central roles in ion homeostasis and in cell signaling events, these channels are involved in a wide variety of physiological activities; for example, muscle contraction, cardiovascular function, hormone and neurotransmitter secretion, and tissue growth and remodeling processes. Multiple types of calcium channels have been identified in mammalian cells from various tissues, including skeletal muscle, cardiac muscle, lung, smooth muscle and brain. Not surprisingly, calcium channels are recognized as important targets for drug therapy (See Nuccitelli, R., Methods in Cell Biology: A Practical Guide of the Study of Calcium in Living Cells, Vol. 40, Academic Press (1994); also U.S. Pat. No. 6,686,193). They are implicated in a variety of pathologic conditions, including, for example, essential hypertension, angina, congestive heart failure, arrythmias, migraine and pain.

The disclosures of all documents referred to throughout this application are incorporated herein by reference.

The foregoing examples of the related art and limitations related therewith are intended to be illustrative and not exclusive. Other limitations of the related art will become apparent to those of skill in the art upon a reading of the specification and a study of the drawings.

SUMMARY OF THE INVENTION

The following embodiments and aspects thereof are described and illustrated in conjunction with compositions and methods which are meant to be exemplary and illustrative, not limiting in scope. In various embodiments, one or more of the above-described problems have been reduced or eliminated, while other embodiments are directed to other improvements.

Ion oscillations are known to occur in many cell types and these oscillations and their underlying mechanisms are important for understanding cellular physiology as well as for screening for novel drug treatments. In various embodiments, instrumentation, methods and systems of monitoring ion oscillation in a cell are provided. In other embodiments, methods of creating ion oscillation dose-response curves for a single cell and a cell sample are provided.

Another embodiment by way of non-limiting example includes methods of determining the parameters for imaging a sample. This method involves a determination of the minimally required spatial resolution, spectral resolution and temporal resolution.

Another embodiment by way of non-limiting example includes methods of measuring ion oscillation of a cell that results from dose-dependent administration of a composition. This method involves administering a composition to a cell and monitoring the cell to measure ion oscillation.

Another embodiment by way of non-limiting example includes the methods wherein the cell is administered an ion sensor. In this manner, ion oscillation may be monitored and measured using imaging instrumentation.

Another embodiment by way of non-limiting example includes an apparatus for monitoring and measuring calcium oscillation in a cell, the apparatus being a fluorescence microscope wherein the spatial resolution of said microscope, spectral resolution of said microscope, and temporal resolution of said microscope are separately adjustable for excitation and emission.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION

Figure 1A:
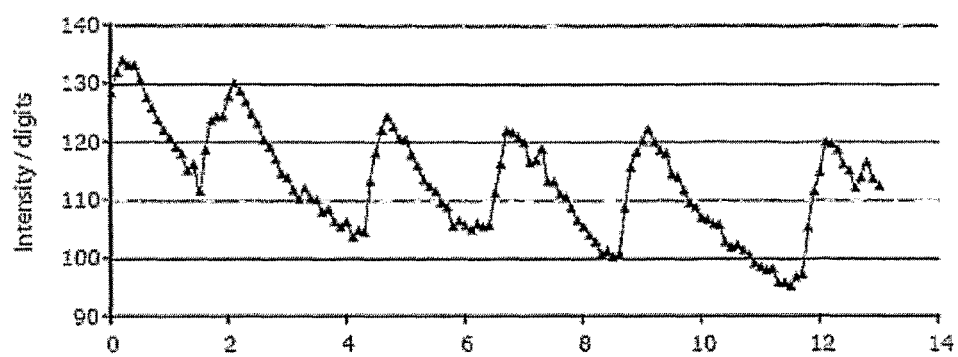
FIG. 1A shows a plot of sampling frequencies of spontaneous calcium oscillations recorded at 10 frames per second (fps). The results show that oscillations are clearly resolved at 10 fps.

The embodiments discussed herein are based on instrumentation and methods to measure and observe ion oscillation dose-response in single cells. In various embodiments, the instrumentation and methods can be used to measure and observe any biological process in which ion oscillations can be modulated by dose-dependent drug administration. In various embodiments, the instrumentation and methods can be used to image a fluorescent cell sample while preventing photobleaching and allowing observation of cellular response to dose-dependent drug administration. In various embodiments, the instrumentation and methods minimizes spatial resolution and maximizes sensitivity to resolve ion oscillations; thereby providing diffraction limited point illumination for wide-field detection. In various embodiments, drug candidate screening methods are applied to discover compounds or agents with activity against ion channel targets. The embodiments discussed herein can be distinguished from other available techniques in that the instrumentation and methods are fast and cost efficient; for example, the dose-dependent experiments explained herein can be completed in one hour as opposed to the two days which is typically required using the patch-clamp technique.

The methods and instrumentation described herein are useful for recording images of ion fluctuations in live cells. In other embodiments, the methods and instrumentation described herein are useful for fluorescence image analysis and signal processing to derive pharmacological benchmarks. In other embodiments, the methods and instrumentation described herein are useful to record ion flux in live cells while applying compound(s) or agent(s) at increasing doses. In other embodiments, the methods and instrumentation described herein are useful for automated drug screening methods. Other useful applications of the methods and instrumentation described herein will be readily recognized by one of skill in the art, and therefore are included herein.

In various embodiments, a high-content cell screening system is provided for imaging ion oscillation of individual cells of a sample. The system can be used with any type of cell, including animal cells, plant cells, insect cells, bacterial cells, yeast and mammalian cells. For example, when screening for human therapeutics, mammalian cell lines could be used including tissue culture cell lines that can be relatively easily grown and can be readily transfected with high efficiency. Many tissue cell lines are commercially available through the American type culture collection (ATCC) and the European collection of cell cultures (ECACC). In various other embodiments, primary cell lines or tissue slices may be used for screening when it is required to express, or measure, the response of the ion channel of interest in its native physiological context. This approach may be useful either as a primary or a secondary screen to screen for specificity, selectivity or toxicity of candidate therapeutics (See, e.g., U.S. Pat. No. 6,686,193). In various embodiments discussed herein, the cell screening system further comprises a chamber and control system to maintain the temperature, $CO_2$ concentration and humidity surrounding the plate at levels required to keep cells alive.

In various embodiments, cells may be selected based on the expression of a particular ion channel of interest. In other embodiments, nucleic acids may be used to transfect cells with sequences coding for expression of an ion channel of interest, which are typically in the form of an expression vector including expression control sequences operatively linked to a nucleotide sequence coding for expression of the channel. Methods which are well known to those skilled in the art can be used to construct expression vectors containing the ion channel coding sequence, operatively coupled to appropriate localization or targeting domains and appropriate transcriptional and translational control signals (See Maniatis, et al., Molecular Cloning A Laboratory Manual, Cold Spring Harbor Laboratory, N.Y., 1989; also U.S. Pat. No. 6,686,193).

In various embodiments, an ion of interest in the individual cells of the sample is labeled with an ion sensor. The term "ion sensor" includes, for example, but is in no way limited to electrochromic transmembrane potential dyes, transmembrane potential redistribution dyes, ion sensitive fluorescent or luminescent dyes, and ion sensitive fluorescent proteins that are capable of providing an indication of the transmembrane potential and/or concentration gradient. Other ion sensors will be readily recognized by one of ordinary skill in the art. In various embodiments discussing ion sensors herein, Calcium Green calcium sensitive dye was used. The advantage over dual excitation ratiometric dyes is two-fold. First, single wavelength excitation reduces exposure to light since only one wavelength is required. Indeed, single wavelength emission maximizes detection sensitivity because one detector captures all emitted photons. Second, the lower excitation wavelength of Calcium Green compared to UV excitation of dual wavelength dyes is less damaging to cells. However, other calcium sensitive dyes are known in the art that are suitable (Grynkiewicz, G. et al., "A generation of $Ca^{++}$ indicators with greatly improved fluorescence properties," *J. Biol. Chem.*, 260:3340-3350 (1985)). For example, a variety of calcium sensitive dyes may be used for ion imaging as described herein including, for example, but in no way limited to, ion selective fluorophores such as Fura-2, Fluo-3, Fluo-4, Indo-1, Calcium Green-1, Calcium Green-2, Calcium Orange, and combinations thereof. Other calcium sensitive dyes will be readily recognized by one of skill in the art, and therefore are included herein (See, e.g., Nuccitelli, R., A Practical Guide of the Study of Calcium in Living Cells, Pt. 3 "Fluorescent Techniques for Imaging Calcium", Academic Press, pp. 184-219 (1994)).

In other embodiments, intracellular or trans-membrane receptors which are involved in ion signaling cascades may be targeted and loaded with a cell permeable ion sensor. For example, G-protein coupled receptors (GPCRs) are a class of trans-membrane domain cell surface receptors that may be loaded with a cell permeable ion sensor. Ligands for GPCRs stimulate a cascade of secondary signals in a cell, which may include, but are not limited to, $Ca^{2+}$ transients, cyclic AMP production, inositol triphosphate ($IP_3$) production and phosphorylation. Each of these signals is rapid, occurring in a matter of seconds to minutes, but are also generic. For example, many different GPCRs produce a secondary $Ca^{2+}$ Signal when activated. Stimulation of a GPCR also results in the transport of that GPCR from the cell surface membrane to an internal, proximal nuclear compartment. In various embodiments, cells with a GPCR with a blue fluorescent protein (BFP) could be loaded with a cell permeable ion sensor.

In various embodiments discussed herein, the system provides methods of identifying an agent that modulates ion oscillation wherein a short sequence of images is taken from individual cells and the images are analyzed for cells exhibiting ion oscillation. An agent is one that modulates any aspect of ion oscillation. In various embodiments, the methods include identifying agents that modulate ion oscillation by contacting one or more test cells or a portion of a cell with a test agent, monitoring the effect(s) of a test agent on ion oscillation, and identifying a test agent as an agent if it has an effect on ion oscillation. In various embodiments discussed herein, an agent is administered in various doses to a cell sample and ion oscillation is simultaneously recorded for each cell. In various embodiments, the cell screening system provides a method of converting a sequence of recorded images indicating fluorescence intensity to dose response curves.

In various embodiments discussed herein, the cell screening system provides a means of determining parameters for imaging individual cells of the sample. The parameters can be modulated to obtain the minimally required spatial resolution, temporal resolution and spectral resolution used to image the sample. The term "spatial" as used herein refers to the immediate plane of focus of an imaged sample (e.g., the pixel area of the imaged region of interest), which allows for the elimination of out-of-focus light or glare. The term "temporal" as used herein refers to the specific amount of time or excitation that a sample is exposed (e.g., the number of frames per second), which allows for the elimination of toxic and photobleaching effects. The term "spectral" as used herein refers to the wavelength of the excitation laser used to illuminate a sample. As a practical matter, the challenge for imaging is to image cells over extended time periods at high frame rate. Indeed, toxic effects can be triggered directly by excitation light or indirectly by toxic products of photo converted (photo bleached) dye molecules. To solve that problem, the cell screening system provides methods for determining the minimally required spatial resolution, temporal resolution and spectral resolution used to image a sample.

The spatial resolution is determined by the size of a cell of interest. In particular, an example method for determining the minimally required spatial resolution is to determine the projected image size of the smallest object to be imaged and set the pixel size to half of that size or smaller. Applying this method to an illustrative example, a sample is placed on the imaging apparatus; the smallest object of interest is imaged to determine its projected image plane size "x". In turn, the optical magnification is adjusted for scanning format resolution (or binning on a CCD array detector) so that each pixel has the size of "x"/2 or smaller. Other techniques for determining the minimally required spatial resolution are known in the art (See, e.g., Martin, L. C., The Theory of the Microscope, Elsevier (1966); Inoue, S., Video Microscopy, Plenum Press (1986)). For the embodiments discussed herein, imaging a large area per pixel resulted in high collection sensitivity that is similar to pixel binning in digital cameras. Pixel binning is a clocking scheme used to combine the charge collected by several adjacent CCD pixels, and is designed to reduce noise and improve the signal-to-noise ratio and frame rate of digital cameras.

The temporal resolution is determined by the minimally required frequency (frames per second) at which ion oscillation can still be resolved. In particular, an example method for determining the minimally required temporal resolution is to determine the "Nyquist" frequency, which is the lowest possible sampling frequency that can be used without introducing significant error and signal anti-aliasing (See, e.g., Boulton, A. A. et al., Voltametric Methods in Brain Systems, Humana Press (1995); Boulton, A. A. et al., Patch-Clamp Applications and Protocols, Humana Press (1995)). The "Nyquist" frequency, which is named after the Nyquist-Shannon sampling theorem, and/or critical frequency are half the sampling frequency for a signal. Using the sampling theorem, aliasing to be avoided if the Nyquist frequency is at least as large as the bandwidth of the signal being sampled (or the maximum frequency if the signal is a baseband signal). In principle, a Nyquist frequency equal to the signal bandwidth is sufficient to allow perfect reconstruction of the signal from the samples.

The spectral resolution is determined by selecting the widest band of wavelength passed through the detector, while rejecting background fluorescence (e.g., caused by the surrounding media) and autofluorescence of the cell. In particular, an example method for determining the minimally required spectral resolution is provided. First, a determination of the maximally acceptable background fluorescence as a percentage of the overall signal is made; this value is the threshold background fluorescence. Second, an area that shows background fluorescence and specific fluorescence is selected. Third, the spectrophotometer wavelength detection window width is narrowed until the background fluorescence is smaller than the threshold value chosen in step one. In this way, the background fluorescence should be undetectable for the experiment. Applying this method to an illustrative example, first, on an 8 bit digitization system there are 256 intensity levels (0-255), meaning that the threshold background fluorescence must be smaller than $1/256$th of the highest specific fluorescence. As such, second, a cell sample is placed on the imager and an area of the cell sample that has specific fluorescence and background fluorescence must be located. Third, while imaging the area, the wavelength detection window on the spectrophotometer is narrowed until all background pixel values turn to $1/256$th of the fluorescence, or practically speaking, zero.

In various embodiments discussed herein, the cell screening system utilized a confocal scanning illumination and detection system. Although limited by the settings of the manufacturer, the sensitivity of the confocal microscope was improved by decreasing the spatial resolution, which was accomplished by opening the detection pinhole to a maximum of 3.5 Airy units (AU) and using a large spectral window for the spectrophotometer. This reduced the out-of-focus background fluorescence and kept light exposure to a minimum, while the excitation path still provided diffraction limited point illumination. In short, the illumination path was diffraction limited (similar to conventional confocal microscopy), while the detection path was wide field for maximum sensitivity. In various other embodiments discussed herein, other imaging instrumentation may optionally be used which allows for greater asymmetric imaging. In various embodiments, to acquire images at sufficient temporal resolution and prevent aliasing artifacts, oscillations were imaged with the maximum scan frequency available (10 fps) and derived from the lowest acceptable scan frequency from the recorded data. The spectral resolution was limited by the provided laser (488 nm wavelength) of the confocal microscope. Other techniques for improving spatial resolution and confocal imaging of ions are known in the art (See, e.g., Nuccitelli, R., A Practical Guide of the Study of Calcium in Living Cells, Pt. 3 "Fluorescent Techniques for Imaging Calcium", Academic Press, pp. 221-261 (1994)).

Figure 6A:
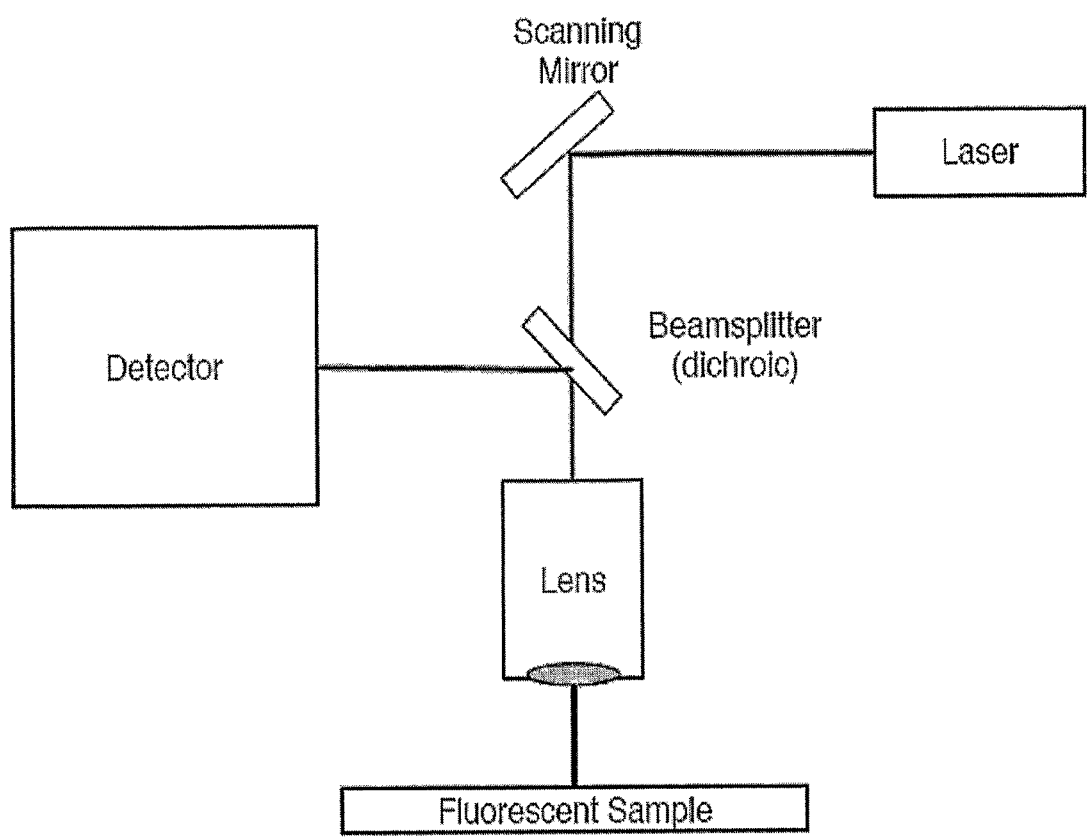
FIG. 6A is a depiction of an illustrative apparatus for imaging ion oscillation consisting of a laser light source, a scanning mirror, one or more dichroic beam splitter(s) and one or more barrier filter(s) and detector(s). The apparatus includes a laser that provides a diffraction limited point light source. The scanning mirror deflects the beam to scan the sample. Illustrative detectors are provided in FIGS. 6B and 6C.
Figure 6B:
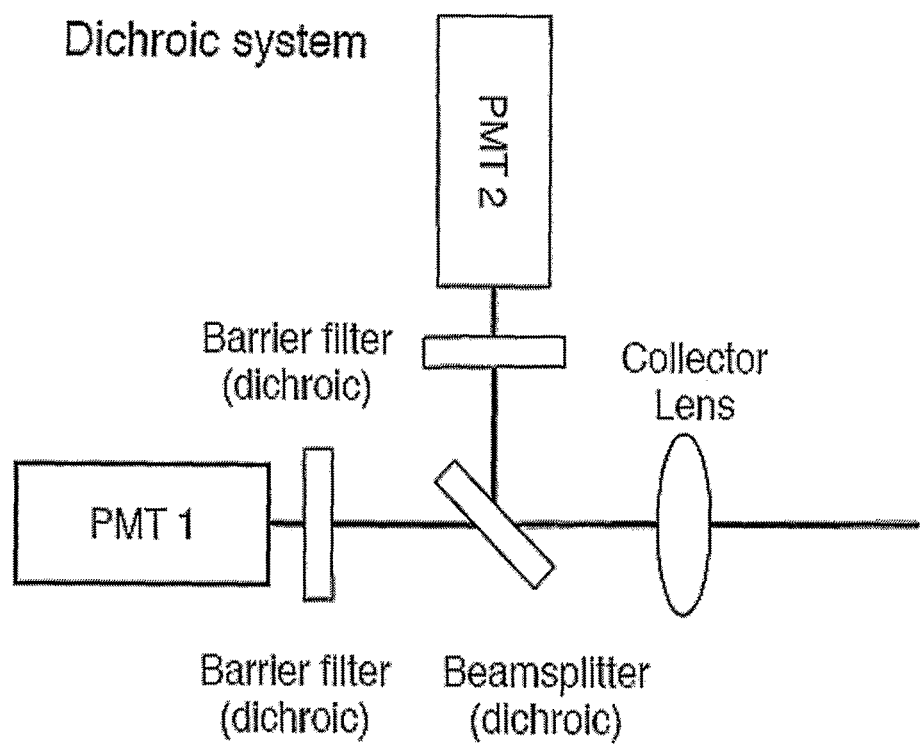
FIG. 6B is a depiction of one embodiment (dichroic system) of the detector of the illustrative apparatus from FIG. 6A in which the emitted light is separated by the beam splitters into different photo detectors. A collection lens is necessary because the detectors are not descanned.
Figure 6C:
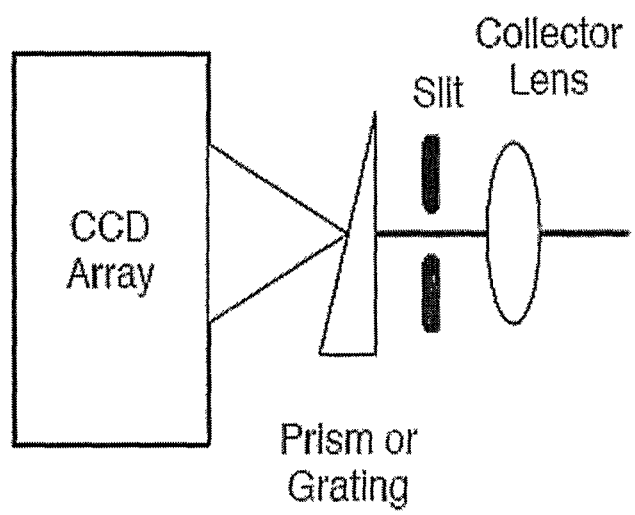
FIG. 6C is a depiction of another embodiment (spectrophotometer) of the detector of the illustrative apparatus from FIG. 6A in which the emitted light goes through a spectrophotometer. A collection lens is necessary because the detectors are not descanned.

In various embodiments discussed herein, an improved apparatus for imaging ion oscillations is provided (FIG. 6A). The apparatus consists of a laser light source, a scanning mirror, one or more dichroic beam splitter(s) and one or more barrier filter(s) and detector(s). In various embodiments, the apparatus includes a laser that provides a diffraction limited point light source. In various embodiments, the scanning mirror deflects the beam to scan the sample. In one embodiment, the emitted light is separated by the beam splitters into different photo detectors (FIG. 6B). In another embodiment, the emitted light goes through a spectrophotometer (FIG. 6C). In various embodiments, a collection lens is necessary because the detectors are not descanned.

To validate the methods described in various embodiments herein, L-type calcium channel dependent changes were measured by applying the L-type channel antagonist nimodipine (Nimotop®; available from Bayer Pharmaceuticals; West Haven, Conn.) with increasing doses and simultaneously recording calcium oscillations for each cell. This allowed for comparison of multiple cells in the same experiment and acquisition of statistical data over larger cell populations. Sigmoidal dose response curves were fit to each individual cell and the average response over the total population was calculated.

Figure 1B:
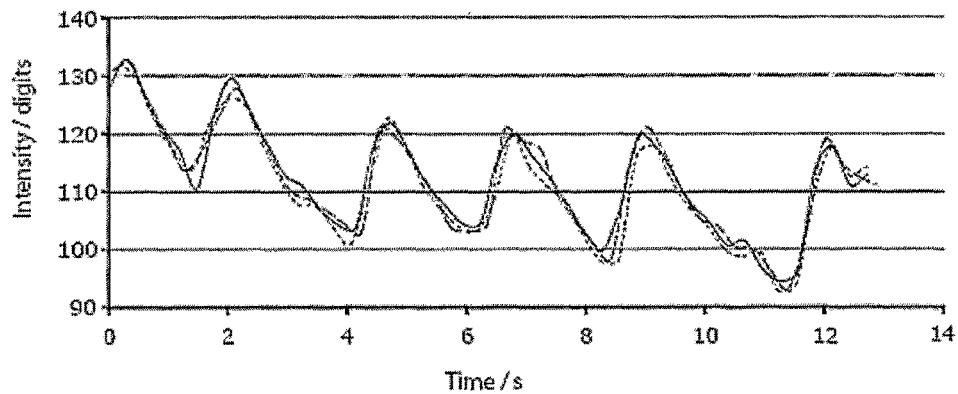
FIG. 1B shows plots of sampling frequencies of spontaneous calcium oscillations downsampled to 3 fps. Three curves were derived from the original data by sampling every third data point and offsetting the subsampling by 1 and 2 values respectively. The results show that subsampling at 3 fps does not introduce significant sampling error, and oscillations are still well resolved.
Figure 1B:
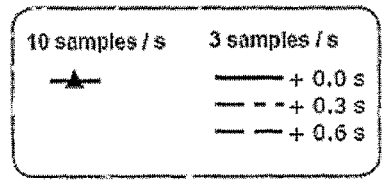

A confocal scanning and detection system was used to validate the methods described in various embodiments herein. In various embodiments discussing the method for determining the parameters for imaging individual cells of a sample, spatial resolution was set to the absolute minimum (128×128 pixels over a 150×150 μm imaging area) allowed by the scanning function. To determine optimal temporal resolution, sampling frequencies of spontaneous calcium oscillations in an untreated cell sample were recorded at 10 fps and the resulting data was plotted (FIG. 1A). FIG. 1A shows that oscillations are clearly resolved at 10 fps. To verify that sampling at 3 fps is still sufficient, three curves were derived from the original data by sampling every third data point and offsetting the subsampling by 1 and 2 values respectively; the resulting data was plotted (FIG. 1B). FIG. 1B shows that subsampling at 3 fps does not introduce significant sampling error, and oscillations are still well resolved. Wavelength resolution was limited by the 488 nm wavelength of the laser on the confocal microscope.

The treated cell samples were imaged using asymmetric imaging methods and a temporal resolution of 3 fps for up to 45 minutes total recording time. In particular, illumination (excitation) was diffraction limited while the detection (emission) was almost wide-field by opening the confocal detection pinhole but leaving the excitation pinhole closed. This allowed for increased detection efficiency, while still suppressing background fluorescence. During the recording time, drug concentrations (nimodipine) were increased over 8 orders of magnitude and intensity fluctuations of fluorescent calcium indicator dye were recorded. In various other embodiments discussed herein, other imaging instrumentation may optionally be used which allows for greater asymmetric imaging, including, for example, but in no way limited to pulsed light sources and nonlinear imaging methods.

In various embodiments discussing the method for determining cell viability herein, to confirm that the imaging system and dye concentration remained stable the quality and validity of the recordings was verified. Calcium Green is a single wavelength calcium indicator and changes intensity significantly with changes in free calcium. However, any change in dye concentration, excitation intensity and detection parameters also creates changes in the recorded intensity. As such, it was confirmed that the imaging system and experimental setup did not produce significant errors. Due to the fact that ratios are inherently resistant to fluctuation in intensity, ratios were verified using calculation methods similar to those described in (Bonnefont, X. et al., "Rhythmic bursts of calcium transients in acute anterior pituitary slices," *Endocrinology*, 141(3):868-75 (2000)). In general, each experiment was divided in 5 minute recording intervals for each drug dose. Calcium oscillations were quantified for each 5 minute interval separately and these intervals were repeated for up to 45 minutes total recording time. The methodology was validated by control experiments for 5 minute intervals and 45 minute intervals. Five (5) minute control experiments verified the quality of imaging excluding artifacts from laser fluctuations, focus drifts and other imaging related problems. Forty-five (45) minute control experiments accounted for long-term changes including detection of changes in cell behavior and long term stability of the imaging system.

Figure 2A:
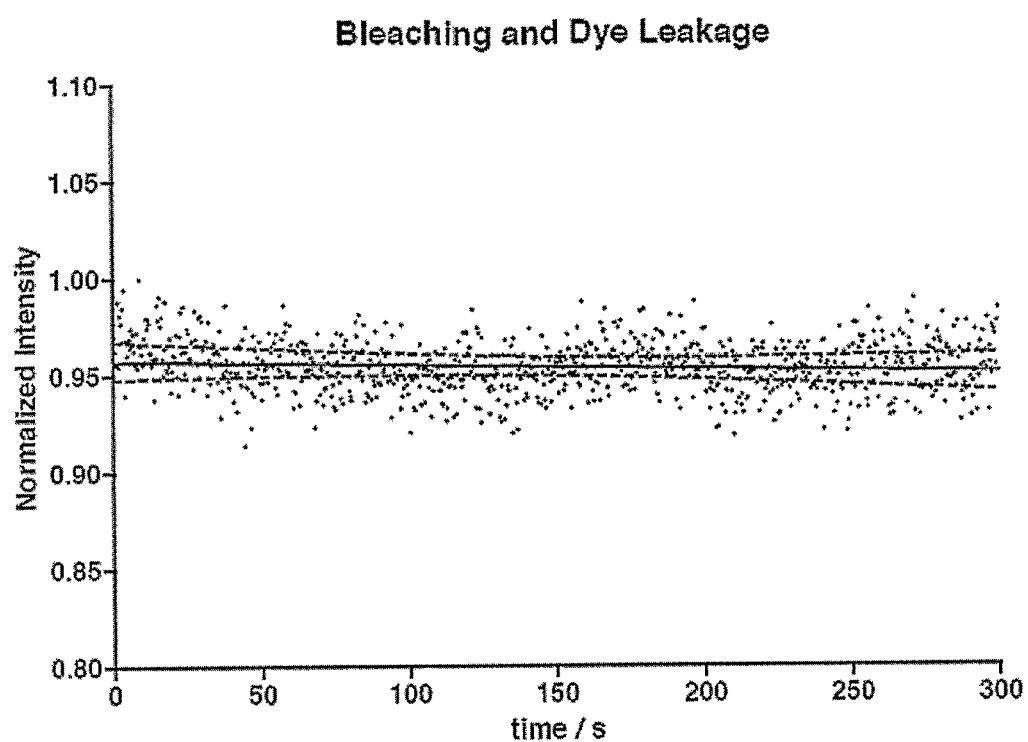
FIG. 2A shows the graphed intensity data for fourteen (14) AtT-20 cells treated with nimodipine to suppress oscillations and imaged over 5 minute intervals at 3 fps. The intensity for each cell was measured for each frame, the raw data points were plotted and because the rate of bleaching and/or dye leakage was very low, a linear correlation curve was fitted to the data. The results indicate that the cells are stable when oscillation is blocked by nimodipine.

At maximum dose of L-channel blocker nimodipine, all oscillations in AtT-20 cells were suppressed. While not wishing to be bound by any theory, if these non-oscillating cells were imaged, then any remaining fluctuation in intensity would necessarily be caused by the imaging system. Indeed, in a perfect system there would be no fluctuations in intensity because changes would induce measurement artifacts. As a practical matter, however, fluctuations that remain significantly below the noise level are sufficient. Fourteen (14) AtT-20 cells were treated with nimodipine to suppress oscillations and imaged for a five (5) minute interval with 3 fps. In various embodiments discussing the 5 minute control experiments herein, the intensity for each cell was measured for each frame, the raw data points were plotted and because the rate of bleaching was very low, a linear correlation curve was fitted to the data (FIG. 2A). The numerical results are summarized in Table 1, as follows:

TABLE 1

| Number of Cells | Number of Image Measurements | Slope 95% Confidence Interval | Deviation from Zero |
|---|---|---|---|
| 14 | 839 | −0.000076 to 0.000034 | Not significant |

Figure 2B:
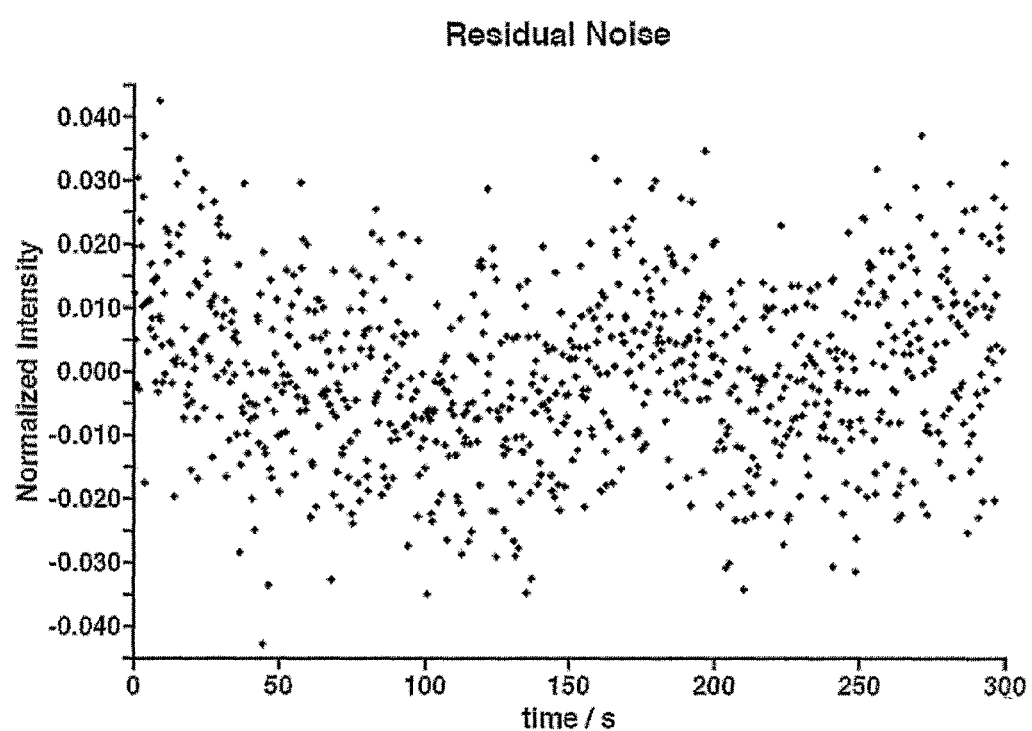
FIG. 2B shows the plotted residual values from FIG. 2A after subtracting a linear curve fit for each data point. The results show an error smaller than 1% with no systematic aberration. From these results, it can be concluded that the instrumentation does not introduce aberrant oscillations.

The rate of bleaching is significantly smaller than 1% for the 5 minute interval. To check for residual errors and deviations, the residual values were plotted after subtracting a linear curve fit for each data point and the results show an error that is smaller than 1% with no systematic aberration (FIG. 2B). Collectively, these results indicated that the instrumental setup did not induce significant measurement artifacts and the dye concentration was stable for each five (5) minute interval.

Cells were stained with Calcium Green, imaged and exposed to increasing drug doses for 45 minutes. In various embodiments discussing the 45 minute control experiments herein, two control experiments were designed to show that these prolonged exposures had no significant toxic effects.

Figure 3A:
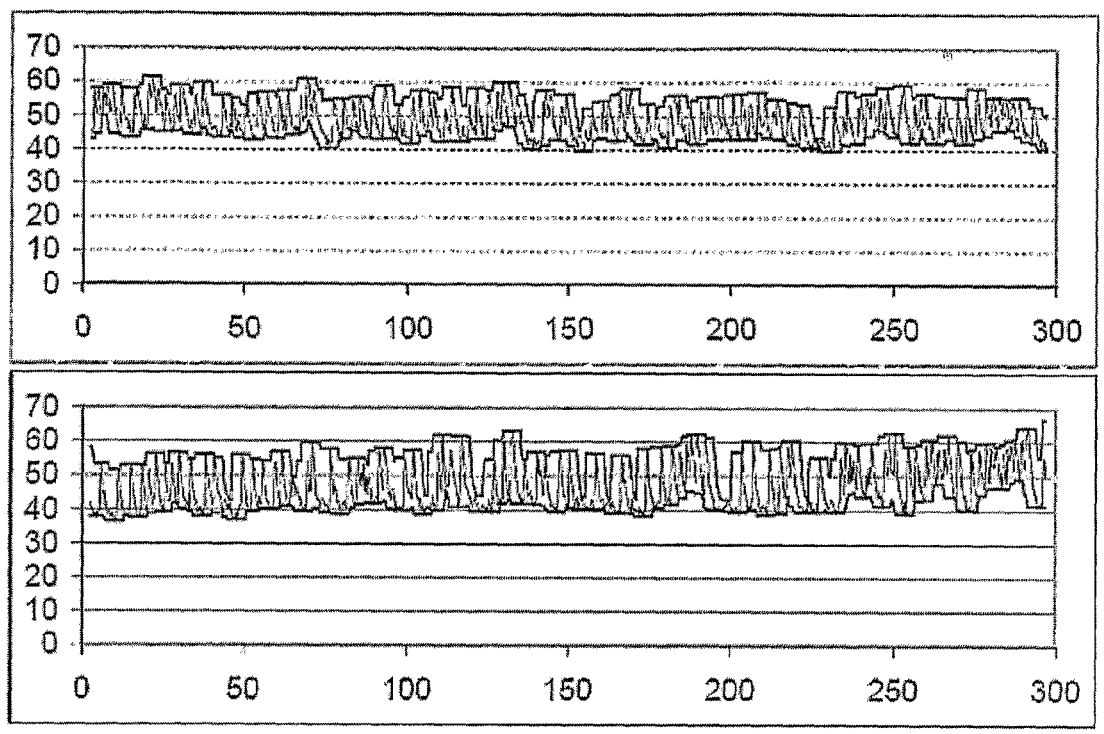
FIG. 3A shows amplitude oscillation traces for a representative untreated cell stained with Calcium Green and continuously imaged at 0 minutes for 300 frames (upper panel) and at 45 minutes for 300 frames (lower panel) at 3 fps. The results show a slight increase in oscillations after 45 minutes but no general change in oscillation patterns.
Figure 3B:
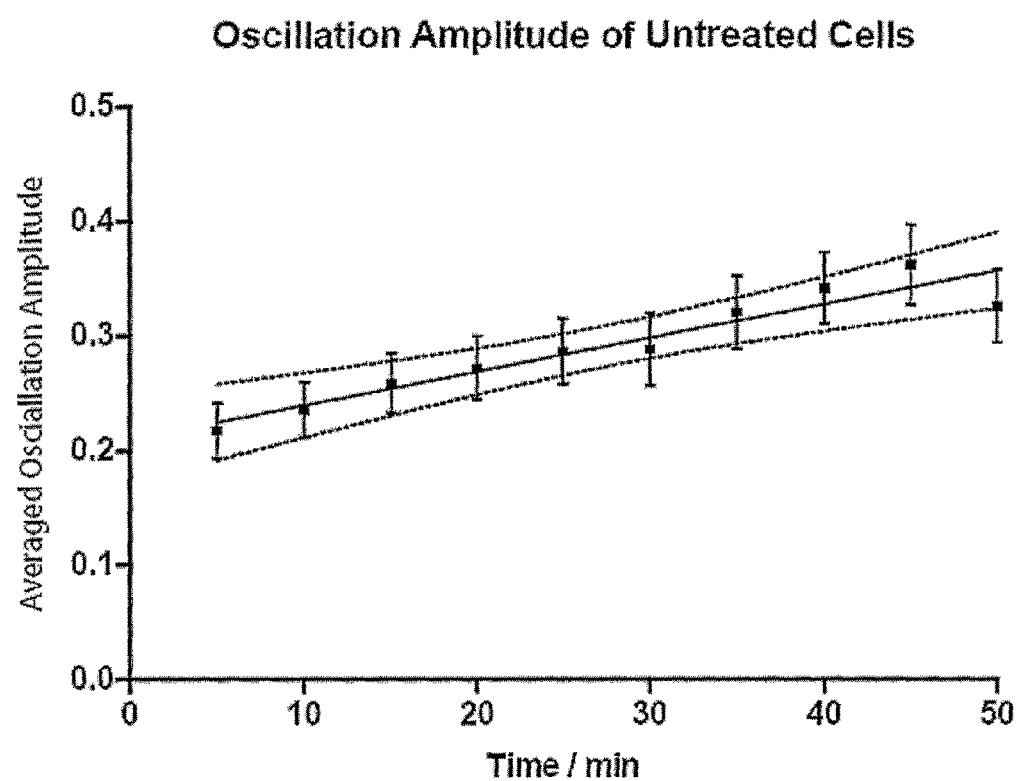
FIG. 3B shows the averaged oscillation amplitudes for a cell sample continuously imaged over 50 minutes at 3 fps. The results show that oscillation amplitudes increase over the first 45 minutes and drop at 50 minutes.
Figure 3C:
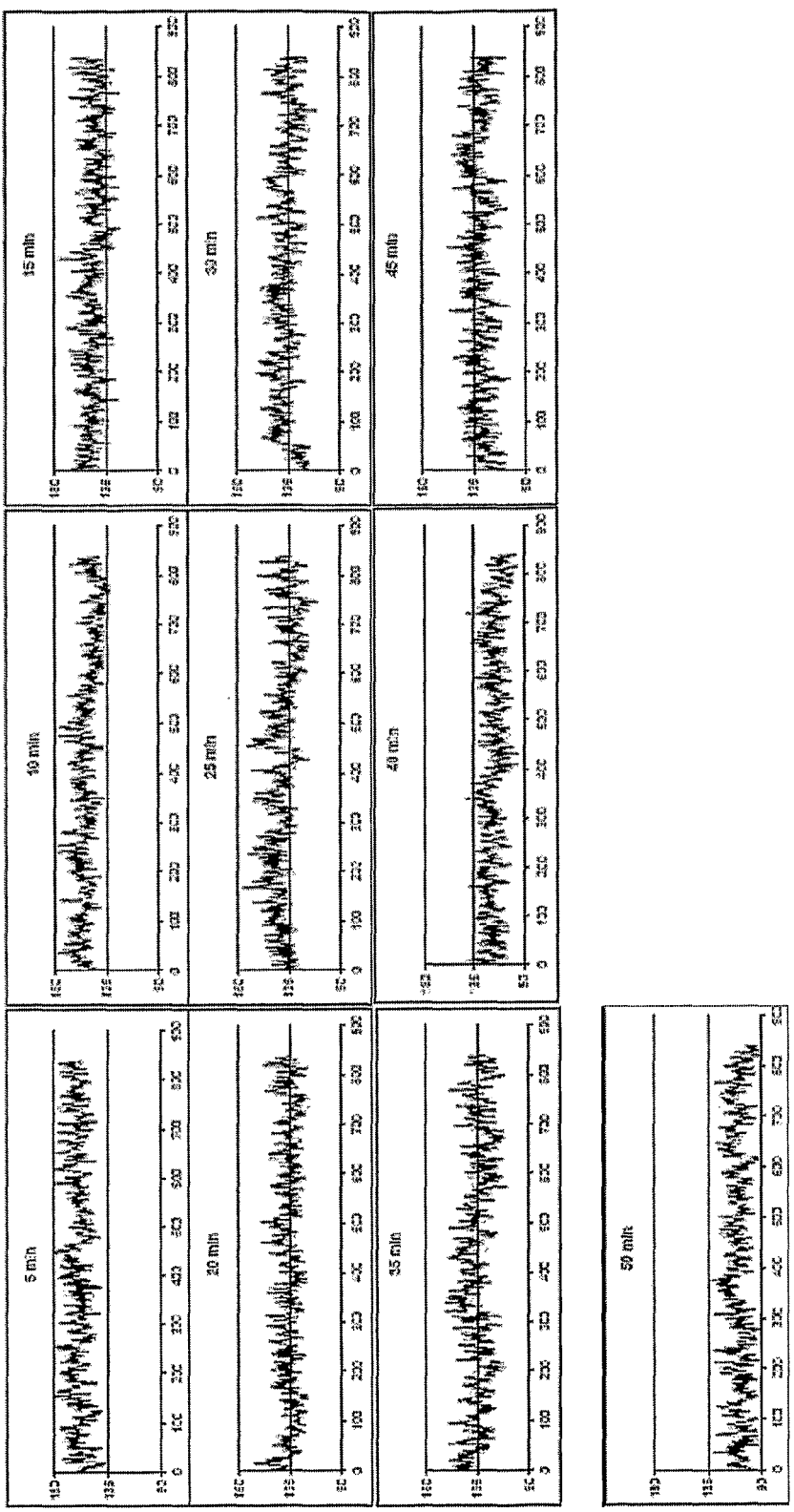
FIG. 3C shows amplitude oscillation traces (5 minute consecutive intervals) for a representative untreated cell stained with Calcium Green and continuously imaged from 0-50 minutes. The X-axis represents recorded frames (scanning rate is 3 frames per second; therefore, 900 frames represent 5 minutes). The Y-axis represents fluorescent dye intensity recorded at a single frame. The sequence of graphs is read from left to right. Intensity of oscillations represents baseline spontaneous calcium oscillations (BSCO). Again, untreated cells display a slight increase in BSCO amplitude, but no pattern change.

First, untreated AtT-20 cells were imaged over a forty-five (45) minute time span with continuous recording at 3 fps. The amplitude of calcium oscillations was measured and plotted over time. The results show that cellular oscillations increase slightly in amplitude over time. However, oscillation patterns remained constant and cells did not exhibit any temporary or transitory changes. The reason for this observation is not clear, and while not wishing to be bound by any theory, it may be explained by the prolonged laser exposure of the cells as suggested in other cell systems (Knight, M. M. et al., "Live cell imaging using confocal microscopy induces intracellular calcium transients and cell death," *Am J Physiol Cell Physiol* 284:1083-1089 (2003)). FIG. 3A shows oscillation traces for a representative cell imaged at 0 minutes and 45 minutes. FIG. 3C shows oscillation traces for a representative cell imaged continuously from 0-50 minutes in 5 consecutive minute intervals. The averaged oscillation amplitudes of an untreated cell sample over a fifty (50) minute interval for all cells is shown in FIG. 3B. Collectively, these results suggest that oscillation amplitudes increase over the first 45 minutes and drop at 50 minutes. While not wishing to be bound by any theory, the drop could indicate the onset of toxic effects. As such, experiments were not recorded longer than 45 minutes.

Figure 4A:
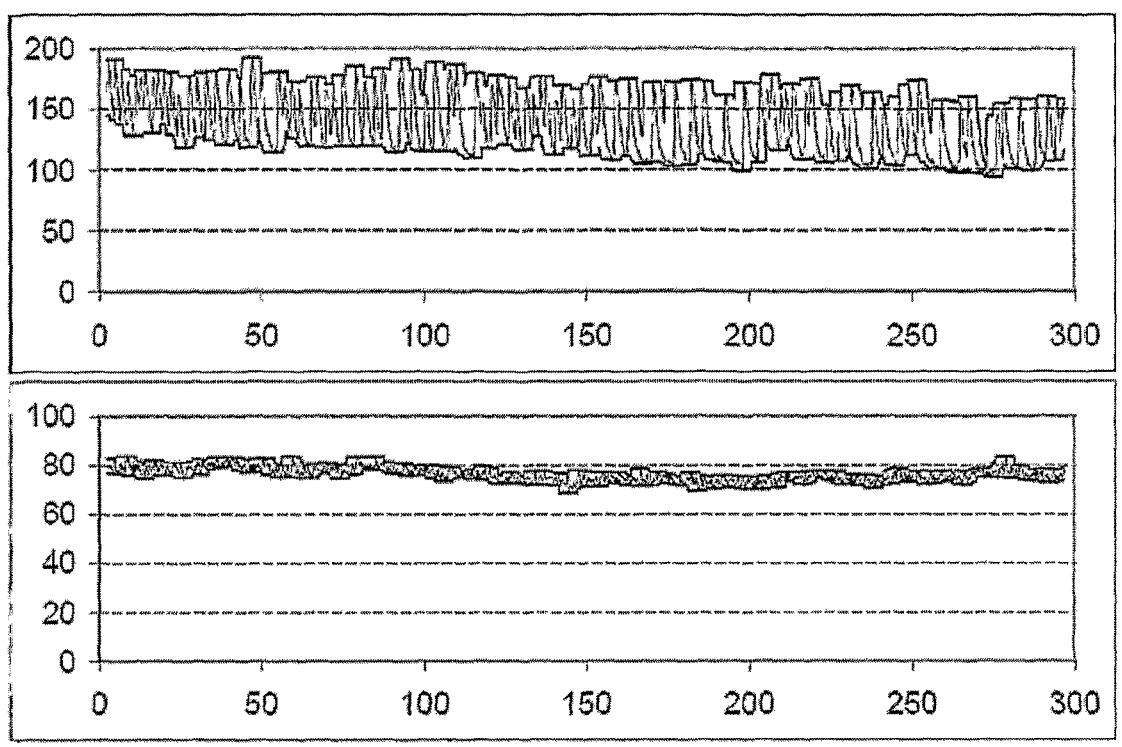
FIG. 4A shows amplitude oscillation traces of a representative cell after treatment with nimodipine, stained with Calcium Green and continuously imaged at 0 minutes for 300 frames (upper panel) and at 45 minutes for 300 frames (lower panel) at 3 fps. The results show that oscillations are significantly depressed and the amplitude is visibly smaller.
Figure 4B:
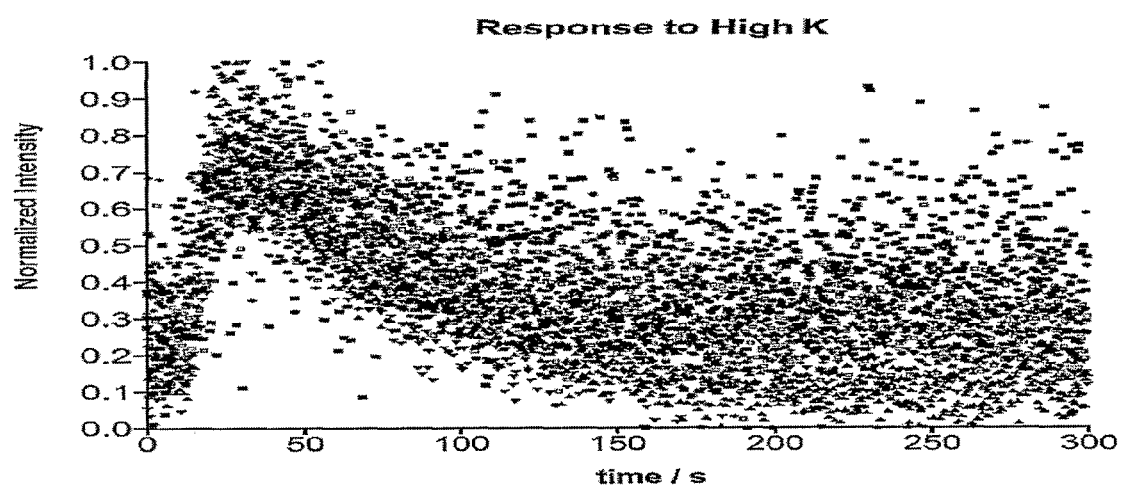
FIG. 4B shows a cell sample calcium response when oscillations were completely suppressed and the membranes were depolarized with high $K^+$. The results demonstrate that cells exposed to 45 minutes of imaging and nimodipine treatment maintained the capacity to respond and keep a physiological balance of free calcium. From these results, it can be concluded that the cells are viable after maximum does of nimodipine without any toxic side effects.
Figure 4C:
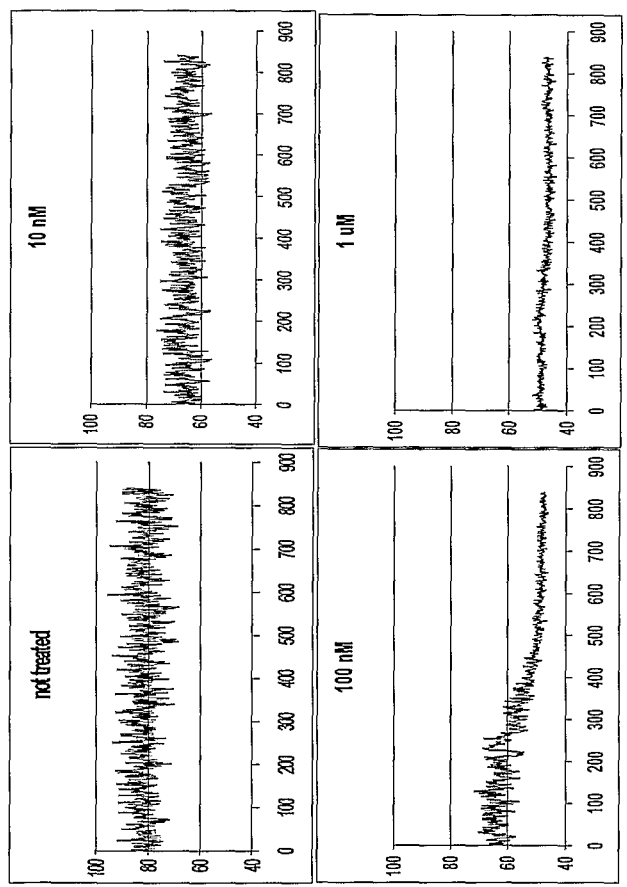
FIG. 4C shows amplitude oscillation traces of a representative cell after treatment with increasing concentrations of nimodipine, stained with Calcium Green and continuously imaged for 5 minutes. The X-axis represents recorded frames (scanning rate is 3 frames per second; therefore, 900 frames represent 5 minutes). The Y-axis represents fluorescent dye intensity recorded at a single frame. The applied concentration is increased by 10-fold increments. The first graph depicts the intensities obtained from the same cell prior to addition of lowest ligand concentration. Nimodipine, the L-type calcium channel blocker, completely inhibits BSCOs at concentrations of 100 nM.

Second, prolonged exposure to nimodipine was confirmed to be non-toxic to cells. FIG. 4A shows oscillation traces of a representative cell before (0 minutes) and after treatment with nimodipine (45 minutes). FIG. 4C shows amplitude oscillation traces of a representative cell after treatment with increasing concentrations of nimodipine, stained with Calcium Green and continuously imaged for 5 minutes. The results show that oscillations are significantly depressed (complete inhibition of BSCOs at concentrations of 100 nM) and the amplitude is visibly smaller. However, to demonstrate that cells still respond when oscillations are completely suppressed, the membrane was depolarized with high potassium ($K^+$) and the resulting calcium response was recorded (FIG. 4B). Healthy cells responded with a transitory increase in intracellular free calcium. However, damaged or dead cells did not show a similar response because the membrane permeability was compromised and calcium channels and pumps were inactive. All cells responded with an immediate but temporary spike in free calcium. The results show that cells exposed to 45 minutes of imaging and nimodipine treatment maintained the capacity to respond and keep a physiological balance of free calcium.

Figure 5A:
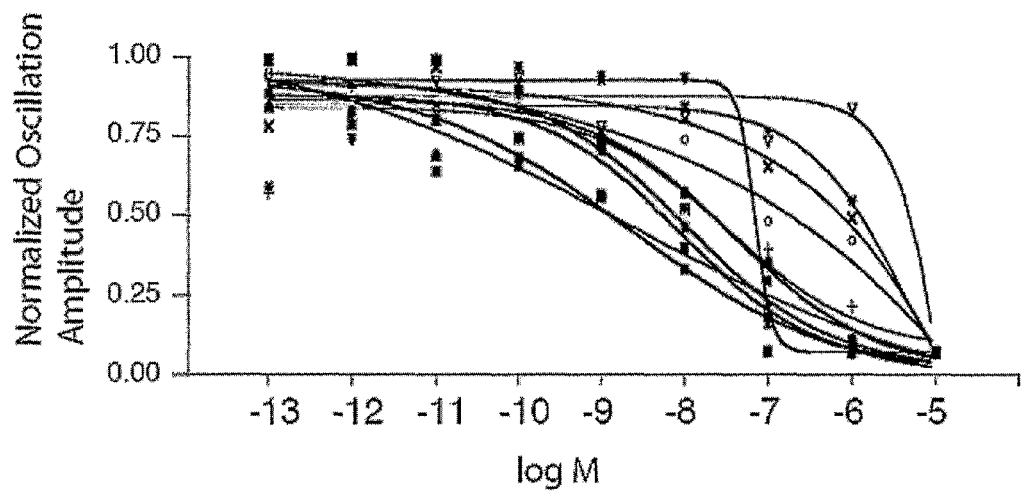
FIG. 5A shows an oscillation plot of the dose response for individual cells treated with nimodipine. The results show that responses vary greatly from cell to cell.
Figure 5B:
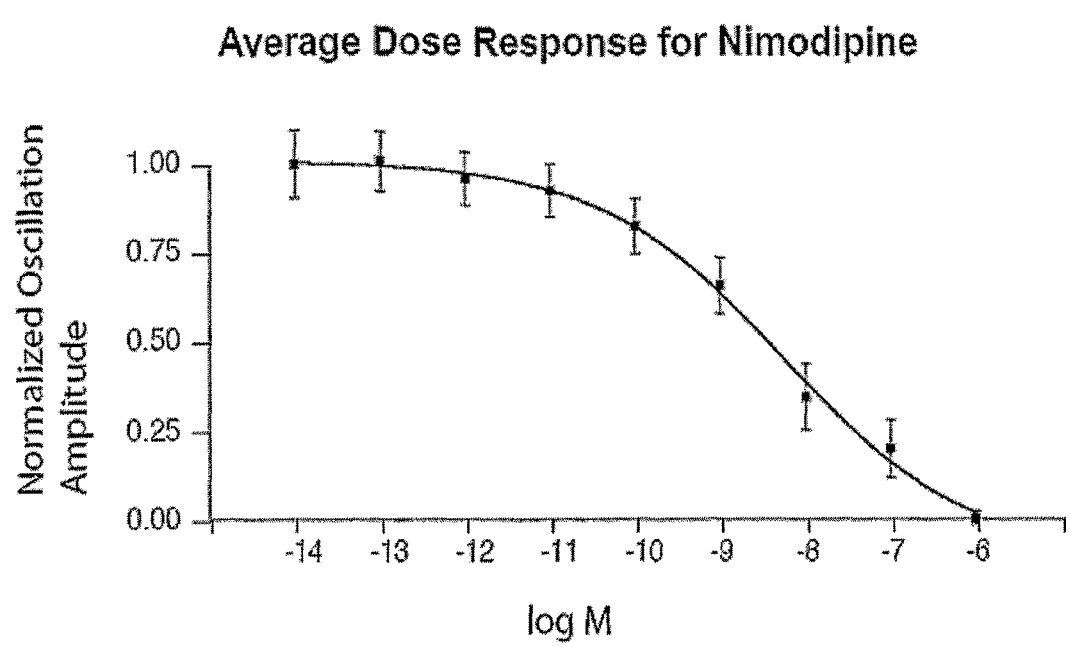
FIG. 5B shows a dose-response curve for the averaged dose response for all individual cells from FIG. 5A. The results show that responses vary greatly from cell to cell, but create a continuum when averaged among the cells.

In various embodiments, a method for converting a sequence of recorded images indicating fluorescence intensity to dose response curves is provided. For example, the dose response for individual cells treated with nimodipine is shown in FIG. 5A. The averaged dose response for all the individual cells treated with nimodipine is shown in FIG. 5B. The $IC_{50}$ is 23 nM. The results indicate that responses vary greatly from cell to cell, but create a continuum when averaged among the cells. Indeed, some cells responded evenly by reducing oscillations over a large range of doses, some cells responded like a threshold switch by shutting down oscillations over only two doses, and some cells reduced oscillations only at very high doses.

In other embodiments of the invention, a variety of calcium channel modulators may be used to validate the methods described herein including, for example, but in no way limited to, DM-BODIPY-dihydropyridine (DMBD), omega conotoxin MVIIA, omega conotoxin MVIIC, Nifedipine (1,4-Dihydro-2,6-dimethyl-4-(2-nitrophenyl)-3,5-pyridinedicarboxylic acid dimethyl ester), (R)-(+)-Bay K 8644 ((4R)-1,4-Dihydro-2,6-dimethyl-5-nitro-4-[2-trifluoromethyl)phenyl]-3-pyridinecarboxylic acid methyl ester), (S)-(−)-Bay K 8644 ((4S)-1,4-Dihydro-2,6-dimethyl-5-nitro-4-[2-trifluoromethyl)phenyl]-3-pyridinecarboxylic acid methyl ester), (±)-Bay K 8644 (1,4-Dihydro-2,6-dimethyl-5-nitro-4-[2-(trifluoromethyl)phenyl]-3-pyridinecarboxylic acid, methyl ester), Conotoxin GVIA, Diltiazem hydrochloride ((2S-cis)-3-(Acetyloxy)-5-[2-(dimethylamino)ethyl]-2,3-dihydro-2-(4-methoxyphenyl)-1,5-benzothiazepin-4(5H)-one), FPL 64176 (2,5-Dimethyl-4-[2-(phenylmethyl)benzoyl]-1H-pyrrole-3-carboxylic acid methyl ester), Gabapentin hydrochloride (1-(Aminomethyl)cyclohexaneacetic acid), [3H]-Gabapentin (1-(Amino-[3H]-methyl)-[2,3,5,6-3H]-cyclohexaneacetic acid), Isradipine (4-(2,1,3-Benzoxadiazol-4-yl)-1,4-dihydro-2,6-dimethyl-3,5-pyridinecarboxylic acid methyl 1-methylethyl ester), Loperamide hydrochloride (4-(4-Chlorophenyl)-4-hydroxy-N,N-dimethyl-a,a-diphenyl-1-piperidinebutanamide), Niguldipine hydrochloride, Nimodipine (1,4-Dihydro-2,6-dimethyl-4-(3-nitrophenyl)-3,5-pyridinedicarboxylic acid 2-methyloxyethyl 1-methylethyl ester), Nitrendipine (1,4-Dihydro-2,6-dimethyl-4-(3-nitrophenyl)-3,5-pyridine dicarboxylic acid ethyl methyl ester), Ruthenium Red Ammoniated (ruthenium oxychloride), SKF 96365 hydrochloride (1-[2-(4-Methoxyphenyl)-2-[3-(4-methoxyphenyl)propoxy]ethyl-1H-imidazole), SR 33805 oxalate (3,4-Dimethoxy-N-methyl-N-[3-[4-[[1-methyl-3-(1-methylethyl)-1H-indol-2-yl]sulfonyl]phenoxy]propyl]benzeneethanamine oxalate), Verapamil hydrochloride (a-[3-[[2-(3,4-Dimethoxyphenyl)ethyl]methylamino]propyl]-3,4-dimethoxy-a-(1-methylethyl)benzeneacetonitrile), and combinations thereof. Other calcium channel modulators will be readily recognized by one of skill in the art.

In principle, calcium fluxes can be modulated in the amplitude (AM) or frequency (FM) domain (Berridge, M. J., "The AM and FM of calcium signalling," *Nature,* 386(6627):759-60 (1997)), as shown in prolactin releasing GH3 cells (Charles, A. C. et al., "L-type Ca2+ channels and K+ channels specifically modulate the frequency and amplitude of spontaneous Ca2+ oscillations and have distinct roles in prolactin release in GH3 cells," *J Biol Chem,* 274(11):7508-15 (1999)). However, the examples presented herein show that oscillations are amplitude and not frequency modulated in a dose-dependent manner by nimodipine. In particular, the characteristic irregular oscillation pattern and frequency did not change, but the relative amplitude of oscillations over free baseline calcium levels was attenuated significantly. Therefore, only changes in amplitude were considered for analysis.

Collectively, these findings indicate that blocking of L-type channels only decreases calcium flux but does not interfere with the pace maker mechanism responsible for the frequency of oscillations. However, responses of individual cells differed considerably in the same experiments. Dose response curves of each individual cell and key parameters such as slope and $IC_{50}$ (drug concentration eliciting 50% of the maximum inhibition) varied significantly from cell to cell. This was a surprising discovery because the cells were clonal and were grown in the same environment and subjected to identical treatment. Consequently, the average dose response over all cells, which is one of the typical calculations made using conventional techniques, depends as much on the statistical distribution of cells as on a genetically predetermined response function.

For the embodiments discussed herein, the individual response characteristics set the boundaries, such as minimum and maximum dose of the response, but the average slope and $IC_{50}$ values derive from the sum of disparate individual responses. Collectively, these findings suggest that the individual cell response characteristics may have patho-physiological and therapeutic implications in a variety of biological models. For example, in various embodiments, a statistical shift in cell populations to cells with different regulatory characteristics in an organism could explain gradual changes in drug responses or progressive changes during degenerative disease and aging. In other embodiments, the methods described herein could have applications for tissue regeneration by stem cells that must be compatible with regulatory characteristics of the original cells. For example, a stem cell therapy designed to supplement the loss of insulin secreting beta cells, which are accompanied by calcium oscillations, in diabetes could be analyzed to see if the regulatory characteristics of the stem cells are compatible with the insulin needs of a target patient. Other applications will be recognized by one of skill in the art, and therefore are included herein.

Cell biology is becoming an increasingly important part of drug discovery. There are a broad array of reagents and assay kits available, including labeling antibodies, dyes, transfection tools, detection probes, various protocols and software-based identification systems. Cell and tissue level assays are used for lead screening, lead optimization, toxicology and target identification and validation applications. The embodiments discussed herein may optionally be used in conjunction with other techniques known to one of skill in the art, including the aforementioned techniques and, for example, but in no way limited to, cyclic AMP (cAMP) assays, fluorescence microscopy, flash photolysis and the patch-clamp technique. Other applications will be recognized by one of skill in the art, and therefore are included herein.

For the embodiments discussed herein, the results emphasize the importance of examining cells individually. Indeed, deviations in statistical distribution cannot be detected with conventional methodologies that average over the complete population of a cell sample.

EXAMPLES

Example 1

Cell Culture

AtT-20/D16-F2 mouse adrenocorticotropic hormone (ACTH)-secreting pituitary cells (CRL-1795; American Type Culture Collection; 2003) were grown in serum-containing low glucose Dulbecco's Modified Eagles Medium (DMEM) (obtained from Invitrogen; Carlsbad, Calif.) supplemented with 10% fetal bovine serum (obtained from Omega Scientifics; Tarzana, Calif.), with addition of 2 mM glutamine and 1% antibiotic/antimycotic (100 U/mL penicillin G sodium, 100 µg/mL streptomycin sulfate, 250 ng/mL amphotericin B (Fungisone® in 0.85% saline); obtained from Invitrogen), in 6% $CO_2$, 37° C. humidified incubator.

For confocal imaging, cells were grown in 6 well plates on 25 mm cover slips coated with 10 µg/ml poly L-lysine (obtained from Sigma Aldrich; St. Louis, Mo.) to 70% confluence in low glucose DMEM with 0.3% Bovine Serum Albumin (BSA) and antibiotics 12 hours prior to analysis.

Ion-imaging cells were stained with Calcium Green-1 AM 488 dye (obtained from Molecular Probes; Eugene Oreg.) according to the instructions of the manufacturer. Briefly, cells were suspended in 1 µM solution of Calcium Green dye aided by the nonionic detergent Pluronic F-127 (10% solution in water) for 30 min. The 25 mm cover slips were transferred to an Attofluor cell culture chamber (obtained from Molecular Probes; Eugene, Oreg.) and filled with 1 ml serum free culture medium.

Example 2

Confocal Cytosolic Calcium Imaging

The Attofluor cell culture chamber was placed inside a PenCon temperature controlled incubator at 37° C. mounted on a DMIRB/E inverted microscope (obtained from Leica Microsystems; Wetzlar, Germany). Cells were imaged with a TCS SP confocal scanner (obtained from Leica Microsystems) using a temperature controlled 63×/1.2 N.A. w/PlanApo water immersion objective. The digital temperature readout of the incubator was checked with a calibrated mercury thermometer to confirm the values within 0.2° C.

For excitation, the 488 nm Argon laser line was used with laser power set to minimum and 488 nm acousto-optic tunable filter (AOTF) line to 9% transmission.

Time lapse sequences were acquired by setting the scanner to medium scan speed, bidirectional scan mode at 128 by 128 pixel resolution, resulting in a scan rate of about 3 fps (350 ms/frame). For the time resolution test, the scan rate was increased to 10 fps by changing to fast bidirectional scan mode. The pinhole was opened to 3.5 Airy units for maximum collection efficiency.

Example 3

Dose Response Acquisition

Cells were imaged over 5 minute time intervals for each dose. Baseline values were acquired with five 5 minute pre-treatment intervals. Consecutively, the drug of choice was added at increasing doses at one order of magnitude increments for each 5 minute interval. Total recording time was 45 minutes. Each 5 minute interval was stored as a separate time series of Tag Image File Format (TIFF) files within the duration of the 45 minute experiment.

Example 4

Measurement and Analysis

Time sequences of images were manually analyzed in Image Processing and Analysis in Java (ImageJ software; obtained from National Institutes of Health; Bethesda, Md.) by importing TIFF files from one 5 minute recording interval (corresponding to a single dose) into a stack. Intensities were measured manually by drawing a region of interest (ROI) around each cell and using the stack profile measurement function. This function measures the average brightness of each ROI over time. The resulting numerical values were transferred into Excel spreadsheets (obtained from Microsoft Corporation; Redmond, Wash.).

The ratio of $(f_{max}-f_{min})/f_{median}$ over a six (6) second sliding time frame was calculated. The calculated ratios over each 5 minute interval were averaged for the final analysis. The resulting table contained the average ratio for each cell and dose as one data point.

These values were transferred to Prism software (obtained from Graphpad Software; San Diego, Calif.) for curve fitting and statistical analysis. For the final results, the amplitude values were normalized and a sigmoidal dose-response curve was fitted with variable slope to either each cell or an average over the population.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. A method of identifying a drug that modulates ion oscillation based upon its effect on ion oscillation in a cell, comprising:
   i. providing a cell sample;
   ii. providing a means of imaging the cell sample;
   iii. administering the drug to said sample, wherein the drug's potential to modulate ion oscillation is unknown prior to administering it to the sample;
   iv. imaging said sample with said means for an interval of time to create a series of images of an ion oscillation response to said drug;
   v. repeating steps i-iv at least five times using different doses of said drug for each repetition;
   vi. measuring the ion oscillation from said images;
   vii. plotting said oscillation for each dose to create an oscillation plot for each single cell of said sample; and
   viii. transforming said plots into a dose-response curve for each single cell of said sample;
   ix. analyzing the dose-response curves and/or oscillation plots to determine the effect of each dose of the drug on ion flux in the cells, wherein individual cell responses are used to determine a minimum and a maximum dose of a response, and an average slope and $IC_{50}$ value are from the sum of disparate individual responses; and
   x. determining that the drug modulates ion oscillation if ion flux is detected, and determining that the drug does not modulate ion oscillation if ion flux is not detected.

2. The method of claim 1, wherein said means of imaging a cell is a fluorescence microscope wherein the spatial resolution of said microscope, spectral resolution of said microscope, and temporal resolution of said microscope are separately adjustable for excitation and emission.

3. The method as in claim 2, wherein said spatial resolution of said microscope, said spectral resolution of said microscope, and said temporal resolution of said microscope are separately adjusted to the minimally required spatial resolution of said microscope, minimally required spectral resolution of said microscope, and minimally required temporal resolution of said microscope.

4. The method as in claim 2, wherein said spatial resolution of said microscope is adjusted using the following steps:
   i. Placing said cell on said microscope;
   ii. Determining the size of the area of said cell to be imaged; and
   iii. Adjusting the magnification of said microscope one half the size of said projected image plane size or smaller.

5. The method as in claim 2, wherein said spectral resolution of said microscope is adjusted using the following steps:
   i. Placing said cell on said microscope;
   ii. Determining the threshold background fluorescence; and
   iii. Adjusting the spectrophotometer wavelength detection window width to image background fluorescence smaller than said threshold.

6. The method as in claim 2, wherein said temporal resolution of said microscope is adjusted using the following steps:
   i. Placing said cell on said microscope;
   ii. Determining the frequency; and
   iii. Adjusting temporal resolution to resolve oscillations.

7. The method of claim 1, wherein said imaging further comprises administering an ion sensor to said cell, establishing the imaging parameters of a microscope, and imaging said cell with said parameters of said microscope for an interval of time to monitor said oscillation.

8. The method as in claim 7, wherein said ion is an ion selected from the group consisting of $Ca^{2+}$, $Ca^+$, $K^+$, $Na^+$, $H^+$, $Cl^-$, $HCO_3^-$, and combinations thereof.

9. The method as in claim 7, wherein said ion sensor is a sensor selected from the group consisting of electrochromic transmembrane potential dyes, transmembrane potential redistribution dyes, ion sensitive fluorescent proteins, ion sensitive fluorescent or luminescent dyes, Fura-2, Fluo-3, Fluo-4, Indo-1, Calcium Green-1, Calcium Green-2, Calcium Orange, and combinations thereof.

10. The method as in claim 7, wherein said ion sensor is Calcium Green dye.

11. The method as in claim 1, wherein said cell is a mammalian cell.

12. A method of identifying a drug that modulates ion oscillation based upon its effect on ion oscillation in a cell sample, comprising:
   i. providing a cell sample;
   ii. providing a means of imaging the cell sample;
   iii. administering the drug to said sample, wherein said drug's potential to modulate ion oscillation is unknown prior to administering it to the sample;
   iv. imaging said sample with said means for an interval of time to create a series of images of an ion oscillation response to said drug;
   v. repeating steps i-iv at least five times using different doses of said drug for each repetition;
   vi. measuring the ion oscillation from said images;
   vii. plotting said oscillation for each dose to create an oscillation plot for each single cell of said sample;
   viii. transforming said plots into a dose-response curve for each single cell of said sample;
   ix. repeating steps i-viii at least two times using different cells from said sample; and
   x. averaging each single cell dose-response curve to create a dose-response curve for said sample; and
   xi. analyzing the dose-response curve and/or oscillation plots to determine the effect of each dose of the drug on ion flux in the sample, wherein individual cell responses are used to determine a minimum and a maximum dose of a response, and an average slope and $IC_{50}$ value are derived from the sum of disparate individual responses; and
   xii. determining that the drug modulates ion oscillation if ion flux is detected, and determining that the drug does not modulate ion oscillation if ion flux is not detected.

13. The method of claim 12, wherein said means of imaging said cell is a fluorescence microscope wherein the spatial resolution of said microscope, spectral resolution of said microscope, and temporal resolution of said microscope are separately adjustable for excitation and emission.

14. The method as in claim 13, wherein said spatial resolution of said microscope, said spectral resolution of said microscope, and said temporal resolution of said microscope are separately adjusted to the minimally required spatial resolution of said microscope, minimally required spectral resolution of said microscope, and minimally required temporal resolution of said microscope.

15. The method as in claim 13, wherein said spatial resolution of said microscope is adjusted using the following steps:
   i. Placing said cell on said microscope;
   ii. Determining the size of the area of said cell to be imaged; and
   iii. Adjusting the magnification of said microscope one half the size of said projected image plane size or smaller.

16. The method as in claim 13, wherein said spectral resolution of said microscope is adjusted using the following steps:
   i. Placing said cell on said microscope;
   ii. Determining the threshold background fluorescence; and
   iii. Adjusting the spectrophotometer wavelength detection window width to image background fluorescence smaller than said threshold.

17. The method as in claim 13, wherein said temporal resolution of said microscope is adjusted using the following steps:
   i. Placing said cell on said microscope;
   ii. Determining the frequency; and
   iii. Adjusting temporal resolution to resolve oscillations.

18. The method of claim 12, wherein said imaging further comprises administering an ion sensor to said cell, establishing the imaging parameters of a microscope, and imaging said cell with said parameters of said microscope for an interval of time to monitor said oscillation.

19. The method as in claim 18, wherein said ion is an ion selected from the group consisting of $Ca^{2+}$, $Ca^+$, $K^+$, $Na^+$, $H^+$, $Cl^-$, $HCO_3^-$, and combinations thereof.

20. The method as in claim 18, wherein said ion sensor is a sensor selected from the group consisting of electrochromic transmembrane potential dyes, transmembrane potential redistribution dyes, ion sensitive fluorescent proteins, ion sensitive fluorescent or luminescent dyes, Fura-2, Fluo-3, Fluo-4, Indo-1, Calcium Green-1, Calcium Green-2, Calcium Orange, and combinations thereof.

21. The method as in claim 18, wherein said ion sensor is Calcium Green dye.

22. The method as in claim 12, wherein said cell is a mammalian cell.

\* \* \* \* \*

UNITED STATES PATENT AND TRADEMARK OFFICE
CERTIFICATE OF CORRECTION

PATENT NO. : 8,709,804 B2
APPLICATION NO. : 11/719085
DATED : April 29, 2014
INVENTOR(S) : Ben-Shlomo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1238 days.

Signed and Sealed this

Twenty-ninth Day of September, 2015

Michelle K. Lee
*Director of the United States Patent and Trademark Office*